United States Patent [19]

Thornton et al.

[11] Patent Number: 5,588,535
[45] Date of Patent: Dec. 31, 1996

[54] SAMPLE PREPARATION SYSTEM FOR SEPARATING WEAR PARTICLES BY SIZE AND MAGNETIC CHARACTERISTICS

[75] Inventors: Michael G. Thornton; Janine M. Thornton, both of Littleton, Colo.

[73] Assignee: Synectic Technology, Inc., Littleton, Colo.

[21] Appl. No.: 322,185

[22] Filed: Oct. 12, 1994

[51] Int. Cl.$^6$ ........................................................ B03C 1/30
[52] U.S. Cl. .............................. 209/38; 209/237; 209/260; 209/355
[58] Field of Search ............................ 209/38, 260, 352, 209/355, 380, 237, 273

[56] References Cited

U.S. PATENT DOCUMENTS

| | | |
|---|---|---|
| 2,105,851 | 9/1936 | Vobach et al. . |
| 3,419,139 | 12/1968 | Agthe ................... 209/237 X |
| 4,047,814 | 9/1977 | Westcott . |
| 4,169,677 | 10/1979 | Luria . |
| 4,550,591 | 11/1985 | Cox et al. . |
| 4,555,331 | 11/1985 | Thornton et al. . |
| 5,059,310 | 10/1991 | Fischer et al. ...................... 209/260 X |
| 5,222,605 | 6/1993 | Pogue ................... 209/260 X |

*Primary Examiner*—D. Glenn Dayoan

*Attorney, Agent, or Firm*—Dorr, Carson, Sloan & Birney, P.C.

[57] ABSTRACT

A system for preparing samples of wear particles employs a series of movable particle traps or screens within a passage to separate particles by size and magnetic characteristics. Movable magnets are placed adjacent to an inlet tube upstream from the particle traps to separate magnetic particles from non-magnetic particles. One embodiment includes a coarse particle trap and a medium particle trap. A controller initially positions the magnets adjacent to the tube and positions both particle traps to block the passage so that only fine non-magnetic wear particles are collected in the first sample. The medium non-magnetic wear particles are then rinsed from the medium particle trap to provide a second sample. Next, the coarse non-magnetic wear particles are rinsed from the coarse particle trap to provide the third sample. The controller once again positions both particle traps to block the passage, removes the magnets, and rinses the magnetic wear particles onto the particle traps so that only fine magnetic wear particles are passed to provide a fourth sample. The medium particle trap is then rinsed to produce a fifth sample containing medium magnetic particles, and the coarse particle trap is rinsed to produce a sixth sample containing coarse magnetic particles. The system can also include an initial trap to prevent oversize particles from entering the passage.

20 Claims, 12 Drawing Sheets

Fig. 10
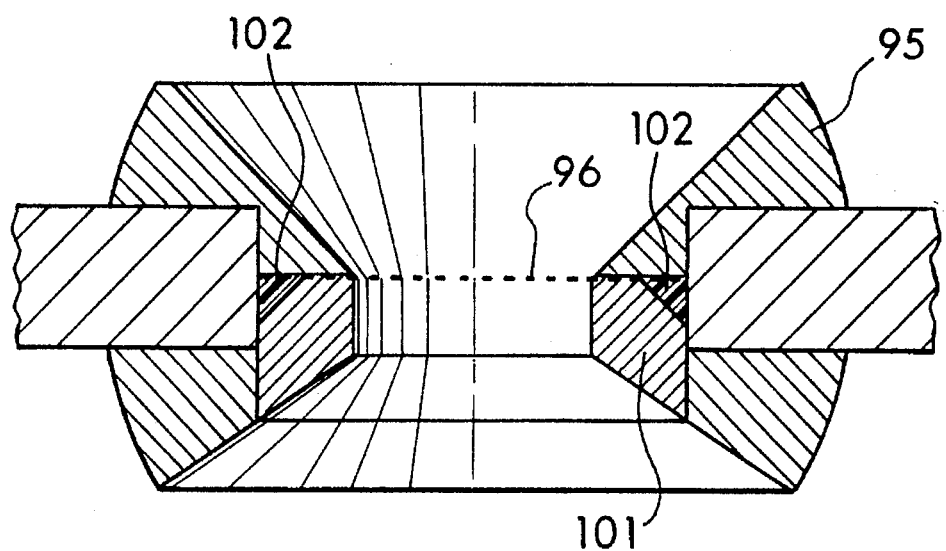
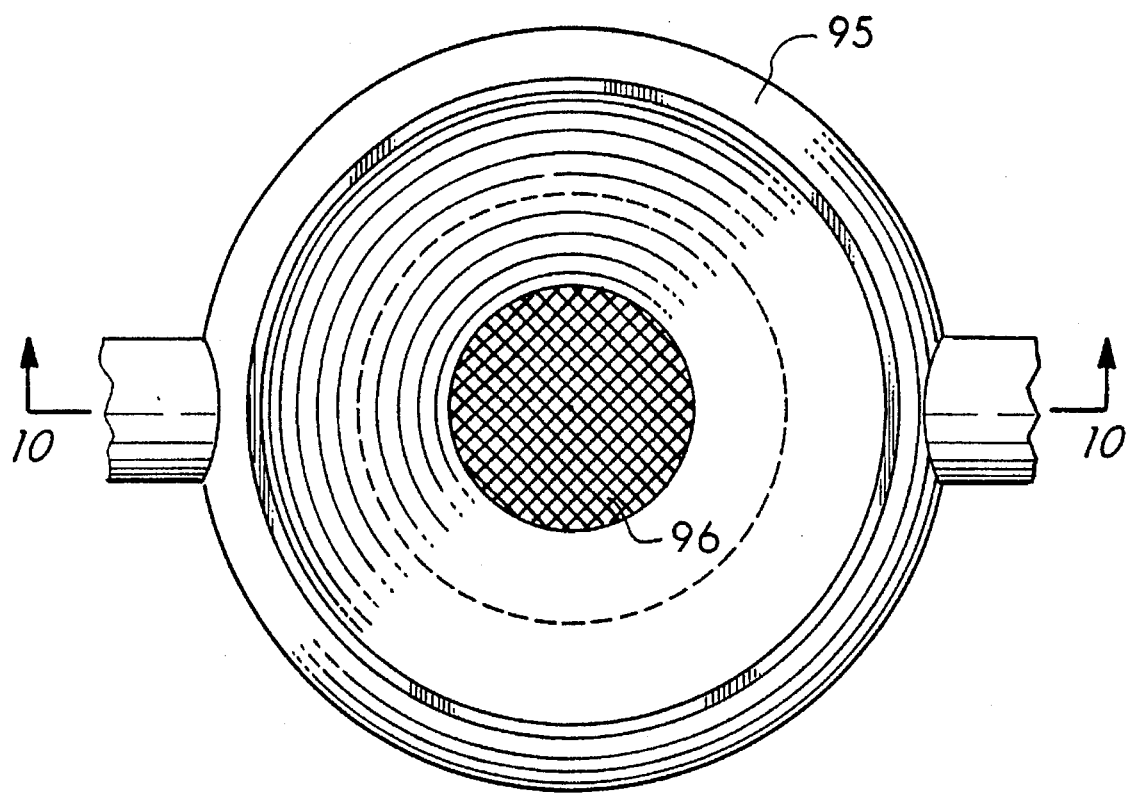
Fig. 11

SAMPLE PREPARATION SYSTEM FOR SEPARATING WEAR PARTICLES BY SIZE AND MAGNETIC CHARACTERISTICS

BACKGROUND OF THE INVENTION

1. Field of the Invention

The present invention relates generally to the field of analyzing wear particles in used lubricants. More specifically, the present invention discloses a sample preparation system for separating wear particles from such fluids by size and magnetic characteristics.

2. Statement of the Problem

The present invention is designed to filter and separate wear particles suspended in used lubricants or hydraulic fluids by particle size and magnetic characteristics. These samples can then be analyzed qualitatively or quantitatively using a conventional energy dispersive x-ray fluorescence (EDXRF) system or other analysis techniques.

More specifically, the present invention is designed to meet the particular needs of the Joint Oil Analysis Program (JOAP) laboratories. These laboratories belong to the Army, Navy, Air Force, and other Department of Defense (DoD) agencies. All of these laboratories are part of an interagency cooperative effort to implement an effective condition monitoring response to threats, and to increase safety of service personnel and the longevity of the hardware transporting the personnel. It is the responsibility of the JOAP Technical Support Center (TSC) to set the equipment standards for analysis for each of the individual condition monitoring and oil analysis programs operated by the Army, Navy, Air Force, and other DoD agencies. If a piece of equipment is to be used in the condition monitoring program of any DoD agency, the analysis system or technique to be used must first receive approval from the JOAP-TSC in Pensacola, Fla.

Current atomic emission spectrographs used by the JOAP are most sensitive to particles having a size of approximately 10 microns or less. Particles larger than 8 to 10 microns in size cannot be vaporized by the high-voltage arc of the atomic emission spectrograph and therefore are not part of the sample analysis. A growing number of people in the engine condition monitoring field are now of the opinion that analysis of a wide range of particle sizes, including larger particles of 10 microns and up, is far more indicative of abnormal wear and provides the best indication of impending, possibly catastrophic failure. This seems reasonable because small metal particles present in the oil are the result of both normal wear and large particles being ground into small particles by the mechanism. Therefore, any analytical technique that is capable of analyzing only small particles is going to be less effective in predicting a need for engine maintenance, and will only occasionally be able to predict the impending catastrophic failures that are most hazardous. It is estimated that current atomic emission spectroscopy techniques detect abnormal wear only an average of once in every 5,000 analyses performed on used oil samples. There have also been several instances where an aircraft has had an in-flight failure shortly after having an oil analysis by atomic emission spectroscopy indicating no unusual quantities of wear metal. Visual inspection of the oil filter and other interior portions of the engines after the crash revealed numerous large particles, chips, and chunks of metal debris. An atomic emission spectroscopy analysis of the used oil collected after the crash still showed nothing abnormal.

An analytical technique that is sensitive to a wide range of particle sizes, including large particles, is advantageous and would allow detection of impending failures that are not observed with the current technique. This translates to a reduction in maintenance costs, increased safety for personnel, and fewer in-flight failures. EDXRF is sensitive to all particle sizes and therefore offers an opportunity to significantly improve the early detection of abnormal wear in aircraft. As a result of these concerns, there is a need for a system to prepare filtration samples in which particles are separated into multiple categories by size and magnetic characteristics. In addition, the system should allow the operator to easily identify any samples containing significant quantities of oversize particles.

Although the present invention was specifically developed to support aircraft engines used for helicopters and jet fighters, it should be expressly understood that the invention is also applicable to analysis of used lubricants and hydraulic fluids from commercial aircraft, ground-based equipment such as heavy construction equipment, trucks, power generation stations, ocean liners, other types of ships, and high performance automobiles.

A number of particle filtration systems have been used in the past for analysis of used oil and lubricants, including the following:

| Inventor | Patent No. | Issue Date |
| --- | --- | --- |
| Thornton et al. | 4,555,331 | Nov. 26, 1985 |
| Cox et al. | 4,550,591 | Nov. 5, 1985 |
| Luria | 4,169,677 | Oct. 2, 1979 |
| Westcott | 4,047,814 | Sep. 13, 1977 |
| Vobach et al. | 2,105,851 | Jan. 18, 1938 |

Thornton et al. disclose a semi-automatic quantitative filtration assembly having means to measure and present a known quantity of fluid for filtering. An in-process fluid holding tank (e.g., moat) adjacent to the filter medium receives any excess fluid during filtering to prevent excess fluid from intermixing with the known quantity of fluid to be filtered.

Cox et al. disclose an apparatus for monitoring particulates in a fluid. The fluid flows through a filter 28. A pressure sensing means 46 senses the fluid pressure difference across the filter. A processor evaluates the rate of change of the pressure difference in order to give an indication of the particulate matter levels in the fluid.

Luria discloses a system for analyzing used oil in which a plurality of samples are separated according to the different mobility rates of its particles through a liquid medium. The samples are separated by passing them through a large mesh screen at the bottom end of a tubular holder in which the centrifuging is effected.

Westcott discloses a system for detecting and analyzing particulate matter suspended in a fluid. The fluid flows over a collecting substrate in the presence of a magnetic or electric field having an intense gradient. The particles are deposited on the substrate in accordance with their size with the larger particles being deposited first and the smaller particles being deposited last.

Vobach et al. disclose a system for measuring contaminants in lubricants. A magnetic field is used to separate magnetic metal particles suspended in the lubricant.

3. Solution to the Problem

None of the prior art references uncovered in the search show a sample preparation system for analysis of wear particles in lubricants that produces filtration samples in which wear particles are separated into multiple categories by size and magnetic characteristics. In addition, the system allows the operator to easily identify any samples containing significant quantities of oversize wear particles.

SUMMARY OF THE INVENTION

This invention provides a system for preparing wear particle samples that employs a series of movable particle traps or screens within a passage to separate particles by size and magnetic characteristics. Movable magnets are placed adjacent to the inlet tube upstream from the particle traps to separate magnetic particles from non-magnetic particles. One embodiment includes a coarse particle trap and a medium particle trap. A controller initially positions the magnets adjacent to the inlet tube and positions both particle traps to block the passage so that only fine non-magnetic wear particles are collected in the first sample. The medium non-magnetic wear particles are then rinsed from the medium particle trap to provide a second sample. Next, the coarse non-magnetic wear particles are rinsed from the coarse particle trap to provide the third sample. The controller once again positions both particle traps to block the passage, removes the magnets, and rinses the magnetic wear particles onto the particle traps so that only fine magnetic wear particles are passed to provide a fourth sample. The medium particle trap is then rinsed to produce a fifth sample containing medium magnetic particles, and the coarse particle trap is rinsed to produce a sixth sample containing coarse magnetic particles. The system can also include an initial trap to prevent oversize particles from entering the passage.

The invention includes design features that: require only minimal training of non-skilled operators to produce consistent results; present oversize large particles to the operator for visual inspection; separate magnetic and non-magnetic particles; separate magnetic and non-magnetic particles by predetermined size ranges; collect the size-graded magnetic and non-magnetic particles on a substrate compatible with EDXRF; provide automatic application of a particle retention fluid to eliminate loss of sample after preparation is complete; provide a self-cleaning rinse system to avoid cross contamination between samples; include safety features to protect the operator; collect all of the fluids extracted from the used oil filter; collect all additional fluids introduced in preparation of samples for easy disposal; provide visual indicators to instruct the operator to perform required actions; prevent operation of the system if inadequate fluid supplies are available to complete a sample preparation; prevent operation of the system if storage capacity is inadequate to capture fluids generated during a sample preparation; and automatically refill internal fluid reservoirs from external supply reservoirs. These and other advantages, features, and objects of the present invention will be more readily understood in view of the following detailed description and the drawings.

BRIEF DESCRIPTION OF THE DRAWINGS

The present invention can be more readily understood in conjunction with the accompanying drawings, in which:

FIG. 10 is a side cross-sectional view of one of the particle trap assemblies within the particle size separation system.

FIG. 11 is a top view of one of the particle trap assemblies within the particle size separation system corresponding to FIG. 10.

DETAILED DESCRIPTION OF THE INVENTION

Overview.

Figure 1:
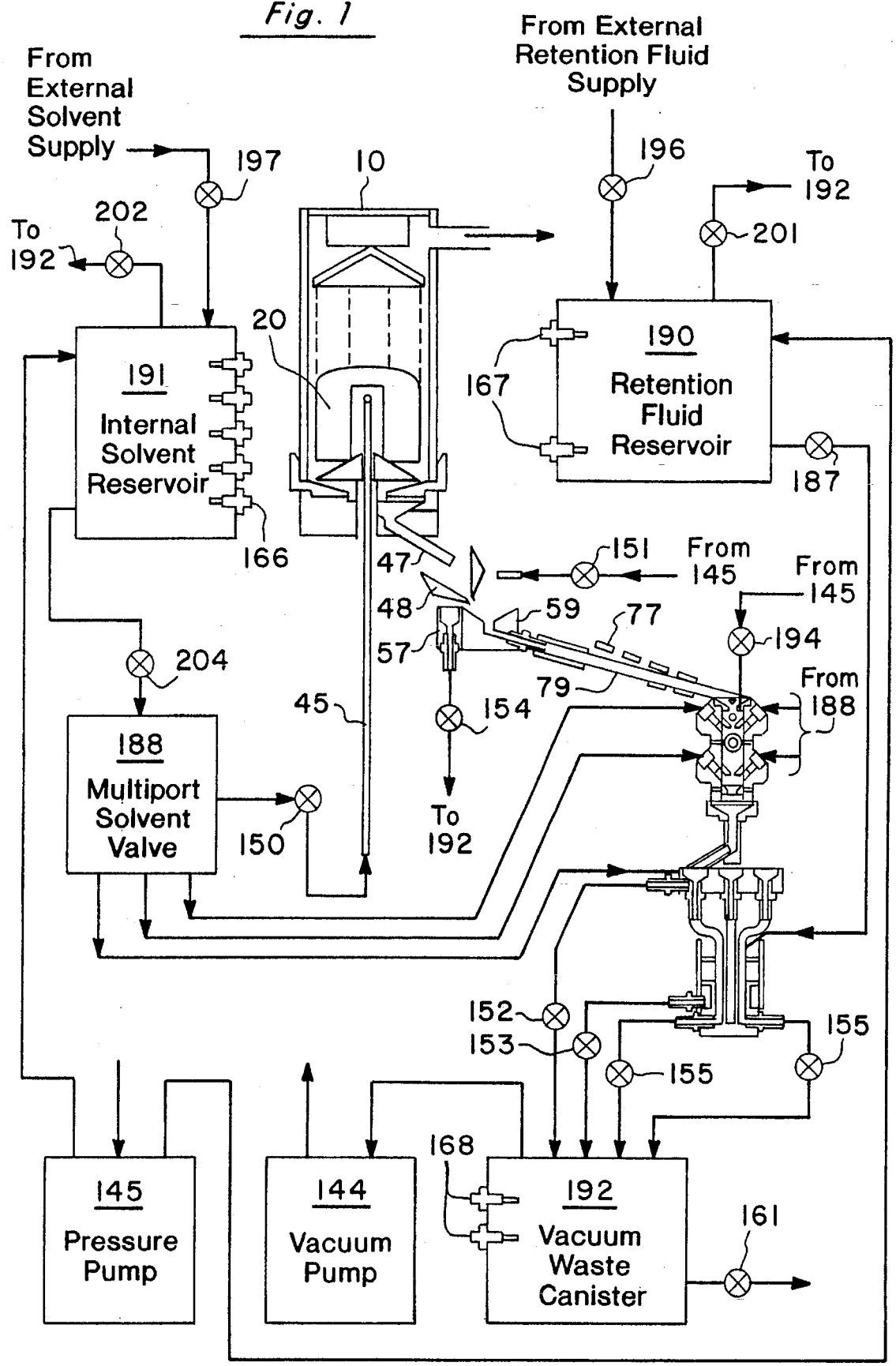
FIG. 1 is a schematic block diagram of the overall system.
Figure 2:
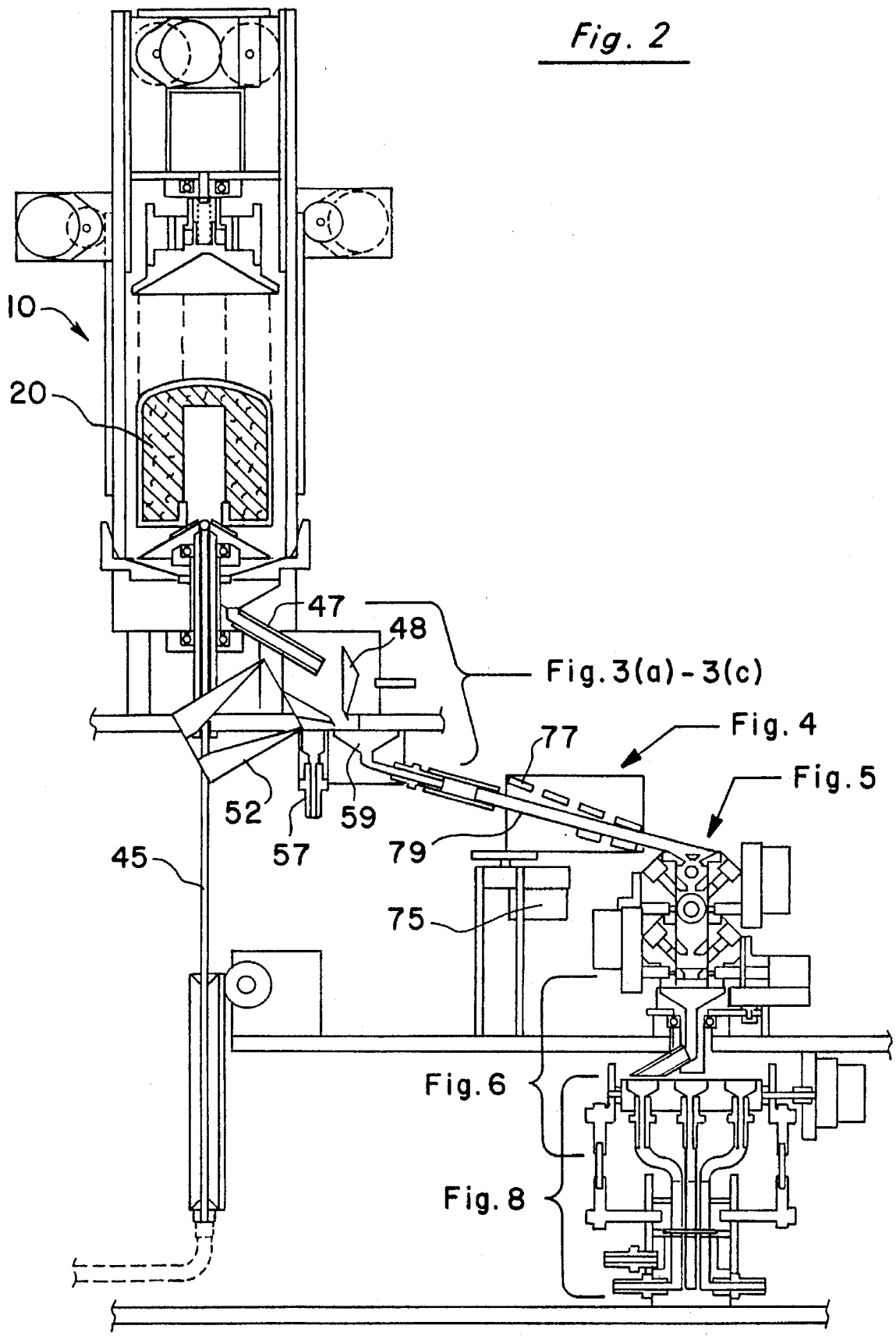
FIG. 2 is a side cross-sectional view of the overall system.

Turning to FIG. 1, a general overview is provided of the entire system. Additional details are illustrated in FIG. 2. The particle removal chamber 10 is used to extract wear particles from a used oil filter 20. This subsystem spins the oil filter 20 at high speed and simultaneously sprays solvent into the interior of the oil filter 20 through a rinse shaft 45. The solvent is delivered from a reservoir 191 and the flow is controlled by a series of valves 204, 188, and 150. The solvent and suspended wear particles drain from the oil filter 20 to the bottom of the particle removal chamber 10 where this material exits through a drain tube 47.

Oversize Particle Trap.

Figure 3A:
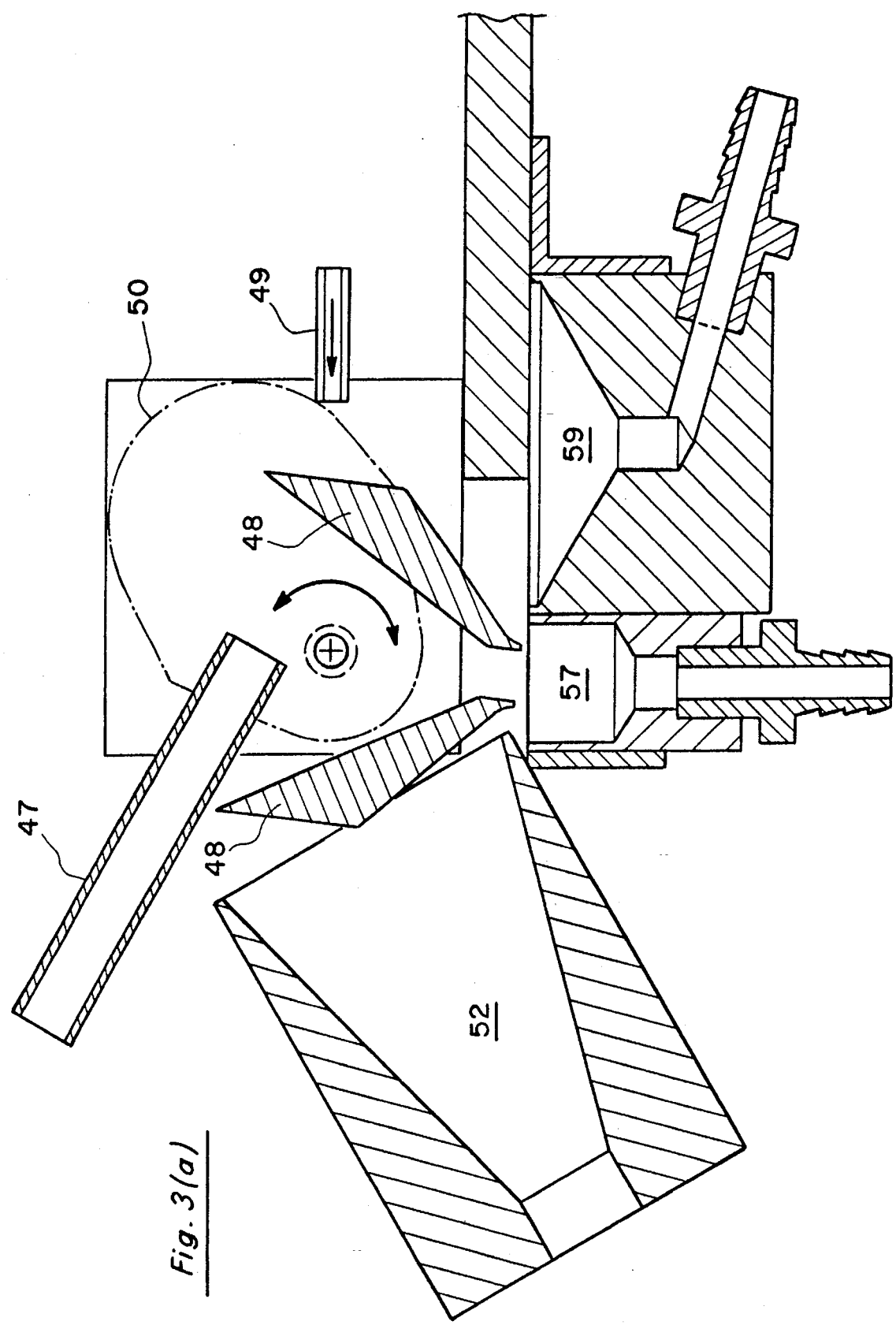
FIGS. 3(a) through 3(c) are detail side cross-sectional views of the oversize particle trap showing the three positions of the funnel 48.
Figure 3B:
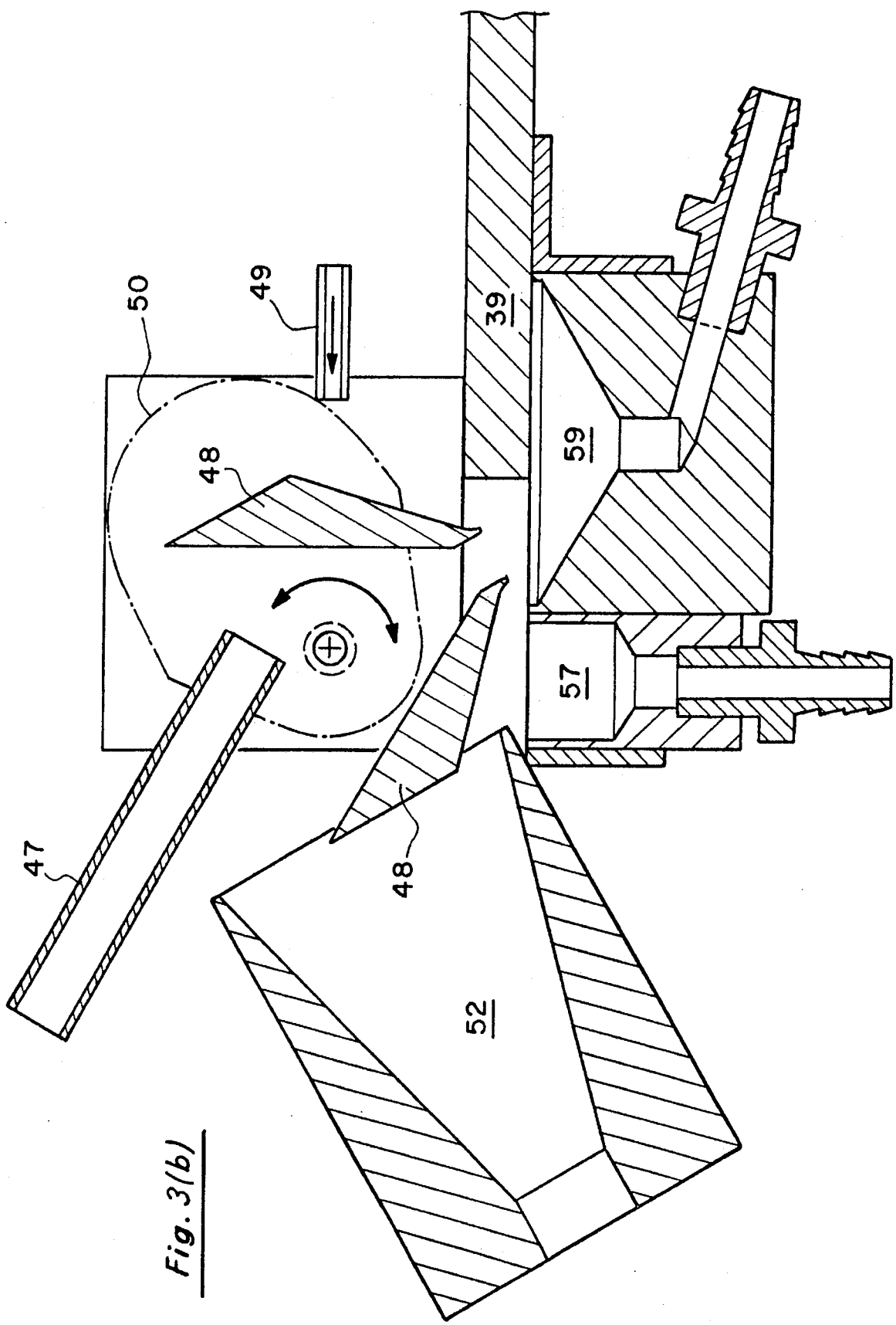
Figure 3C:
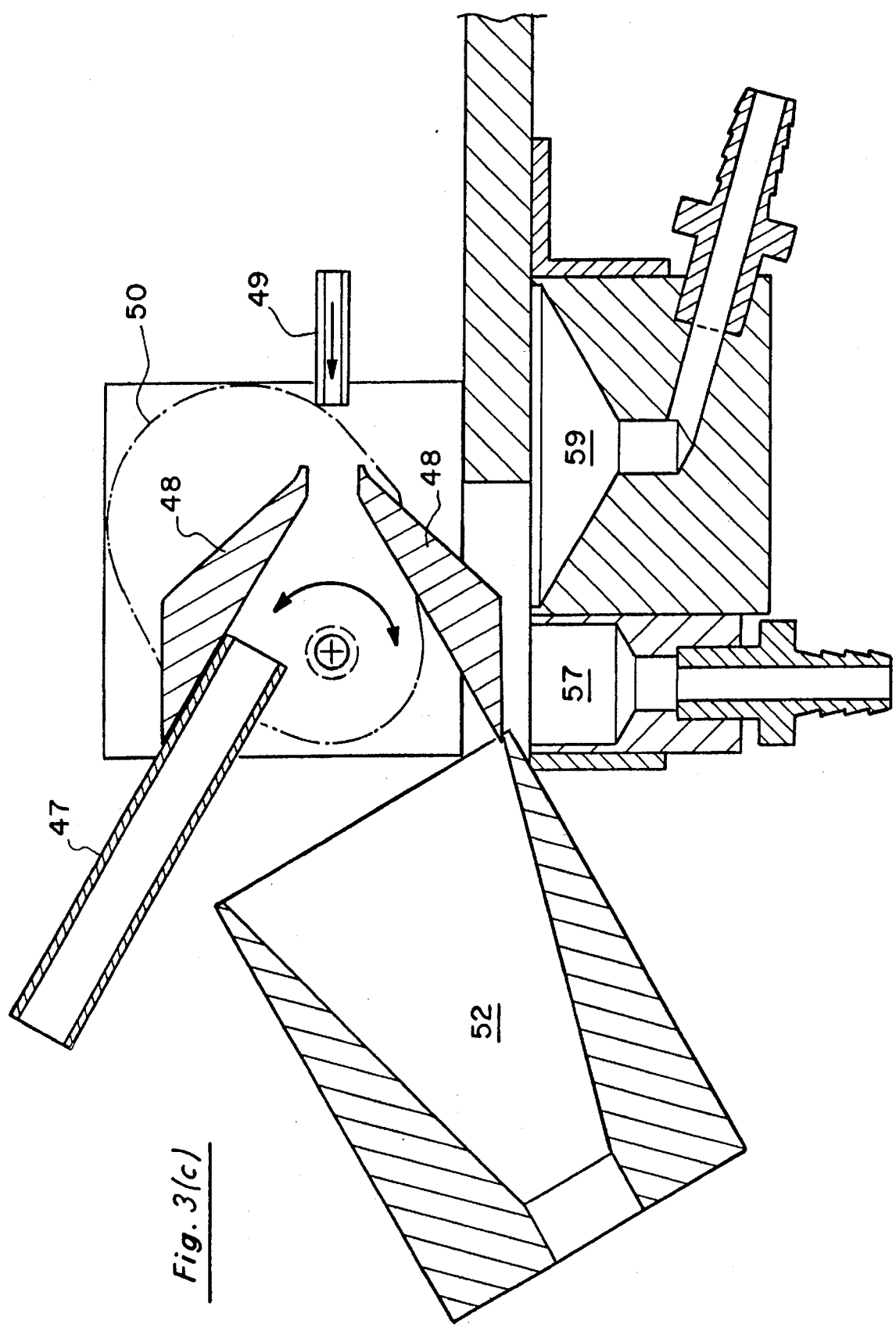

The solvent and wear particles drain into the oversize particle trap shown in FIGS. 3(a) through 3(c). A rotatable funnel 48 driven by a motor 50 is used to trap any oversized particles suspended in the solvent. In particular, the throat of the funnel 48 has a diameter small enough to retain any particles greater than a predetermined size that would otherwise block or damage the downstream components of the system. As shown in FIGS. 3(a) through 3(c), the funnel 48 can be rotated to any of three positions. The first position depicted in FIG. 3(a) allows excess oil or solvent to be drained into a waste drain funnel 57 for subsequent disposal. In one embodiment, a vacuum pump 144 is used to draw the waste fluid into a holding tank or canister 192 through a valve 154 from the waste drain funnel 57, as shown in FIG. 1.

The second position depicted in FIG. 3(b) delivers the solvent and wear particles to a funnel 59 leading to the downstream components of the system for magnetic separation and filtration. The third position shown in FIG. 3(c) is used to eject any oversize particles that have been caught by the rotatable funnel 48. A valve 151 is opened by the control system to release a blast of air from a nozzle 49 to dislodge any oversize particles from the throat of the funnel 48. The oversize particles either roll or are thrown from the funnel 48 into a larger outlet funnel 52. The outlet funnel 52 has a minimum diameter larger than the drain 47, so that all of the oversize particles can pass through the outlet funnel and onto a dish or tray for visual examination by the operator.

Magnetic Separation System.

Figure 4:
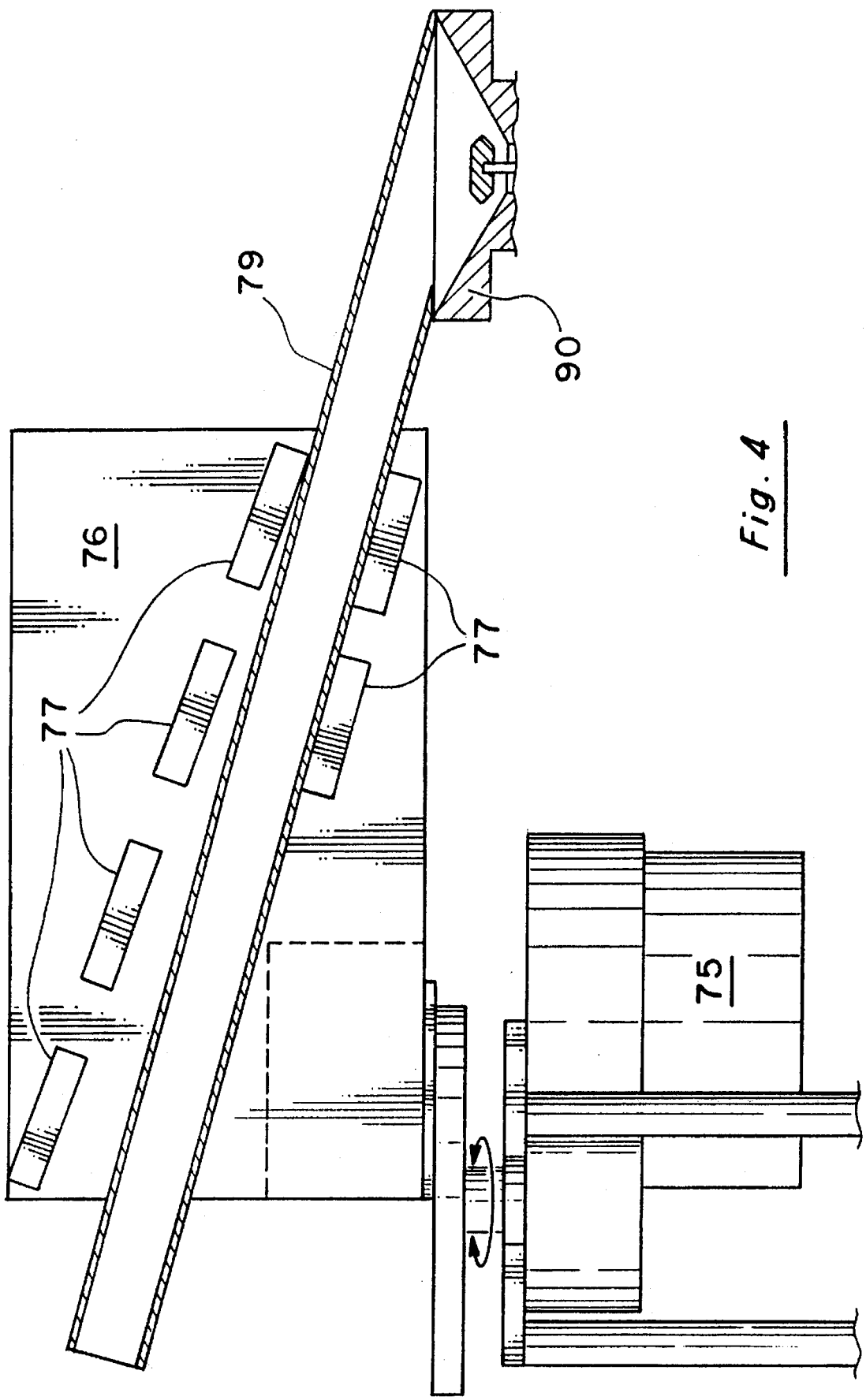
FIG. 4 is a side cross-sectional view of the magnetic particles trap.

Solvent and particles exiting the funnel 59 of the oversize particle trap proceed to the magnetic separation system shown in FIG. 4. This system is designed to temporarily capture all of the magnetic particles removed from the oil filter 20 while allowing the non-magnetic particles to pass through this system into the inlet funnel 90 of the particle size separation system.

As shown in FIG. 4, the mounting plate 76 for the magnets 77 is initially rotated into position by a motor 75 to place the magnets in close proximity to the outer surface of a transparent glass tube 79. Non-magnetic particles pass through the glass tube 79 and enter the inlet funnel 90 to the subsequent filtration stages of the system. Magnetic particles are trapped along the inner surface of the glass tube 79 and can be visually inspected by the operator. After all of the non-magnetic particles have passed through the glass tube 79 and have been processed, the control system releases the trapped magnetic particles by directing the motor 75 to rotate the mounting plate 76 so that the magnets 77 are moved to a position away from the outer surface of the glass tube 79.

The magnetic separation system therefore provides the capability to separate wear particles into magnetic and non-magnetic groups. This feature substantially increases the ability of the EDXRF analysis system to provide more specific information about the alloy composition of the particles. Included in this system are design features to: allow visual inspection of magnetic particles captured; flush non-magnetic particles from the magnetic separation system prior to release of magnetic particles; release magnetic particles into the particle size separation system upon command from the control system; and flush residual particles from this system to prevent cross contamination of subsequent samples.

Particle Size Separation System.

Figure 5:
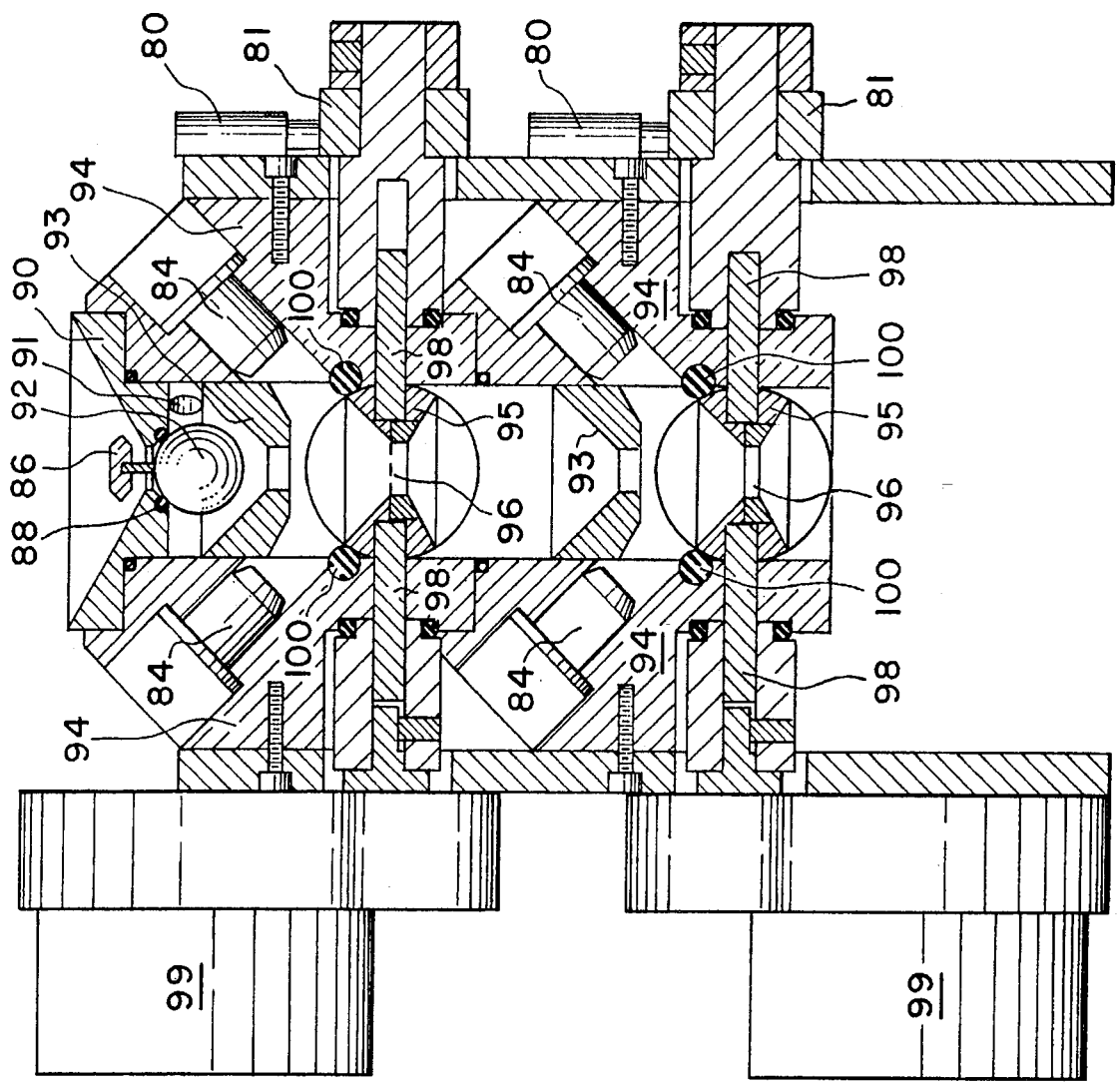
FIG. 5 is a side cross-sectional view of the medium and coarse particles trap.

The particle size separation system separates wear particles into groups by size on a membrane filter compatible with qualitative and quantitative analysis by EDXRF spectrometry. As shown in FIG. 5, the preferred embodiment of the invention incorporates two particle trap assemblies of identical construction that are stacked vertically in a housing 94 along a central passage. These are designated the coarse particle trap and the medium particle trap. The sample of solvent and suspended wear particles flows from the magnetic separation system through an inlet funnel 90 into the housing passage. Each particle trap consists of a screen sieve 96 having a plurality of openings that retain wear particles larger than a predetermined size and pass fluid and any wear particles smaller than the critical size.

FIG. 10 provides a side cross-sectional view of one of the particle trap assemblies corresponding to the detail top view of the assembly shown in FIG. 11. Each screen sieve 96 is held by a pivotable mount 95 within the housing passage so that it can be selectively moved between a first position in which the screen sieve 96 substantially blocks the passage and a second position in which the passage is unblocked. As shown in FIGS. 10 and 11, the mount 95 is generally circular with a diameter substantially equally to that of the housing passage. The rotational orientation of the mount 95 is controlled by a motor 99 that drives a shaft 98 attached diametrically across the mount 95. The screen sieve 96 extends across the central opening in the mount 95. In one embodiment, the screen sieve 96 is held in place by an adhesive bond 102 and an annular retainer 101 that is inserted from the underside of the mount 95 as illustrated in FIG. 10.

Returning to FIG. 5, an O-ring 100 seals the path of fluid and particle flow around each screen sieve 96 within the housing passage when in the first position. The control funnel 93 within each particle trap directs the flow of fluid and extracted particles toward the center of the screen sieve 96. In the preferred embodiment, the position of the screen sieve 96 is controlled by a motor 99 which drives the shaft 98 attached across the diameter of the mount 95 holding the screen sieve 96. A sensor 80 permits the control system to monitor the actual position of the screen sieve by detecting a series of detents in a rotating disk or a gear blank 81 that rotates with the shaft 98.

After the solvent and non-magnetic particles in the sample have entered the inlet funnel 90, a valve 194 connected to the pressure pump 145 is actuated causing a nylon sphere 92 to be pushed into contact with an O-ring 88 to seal the nylon sphere. This allows air pressure to increase the flow rate through the particle trap assemblies by creating a positive pressure differential across both screen sieves 96. A retainer 86 limits the downward motion of the nylon sphere 92 and ensures that fluid flow through the control funnel 93 is not blocked by the nylon sphere 92. The retainer 86 also provides a means to ensure that the nylon sphere 92 is sufficiently close to the O-ring 88 to quickly make a good seal when the valve 194 from the pressure pump 145 is actuated to introduce pressurized air into the particle trap assemblies.

In one alternative embodiment, the position of the nylon sphere 92 is directly controlled by a solenoid connected to the sphere by a shaft that vertically extends upward through the opening in the inlet funnel 90. The retainer 86 shown in FIG. 5 would be redundant in this embodiment and can be eliminated because the range of motion of the sphere 92 is limited by the solenoid. The positive control exercised by the solenoid decreases the response time for the nylon sphere 92 (i.e., the solenoid decreases the time needed for the sphere 92 to seal against the O-ring 88 prior to pressurization, and also decreases the time needed for the sphere to unseal to allow fluid to enter for the next cycle). This decreases the time required by the particle size separation system to process each sample and thereby increases the capacity of the system to handle a large number of samples during a typical working day.

While the preceding discussion identifies two particle trap assemblies, the concepts disclosed are directly applicable to similar devices requiring additional size gradations. The present invention is equally applicable to a sample preparation system incorporating either more or fewer particle trap assemblies. Incorporation of additional particle trap assemblies would also require expansion of the number of funnels in the funnel plate 113 and a corresponding increase in the number of individual filtration columns 129. In a system having more than two particle trap assemblies, the assemblies would normally be stacked in series with the coarsest trap at the top, nearest the inlet. The remaining particle traps are arranged beneath so that the particle traps become progressively finer toward the bottom of the column.

Figure 6:
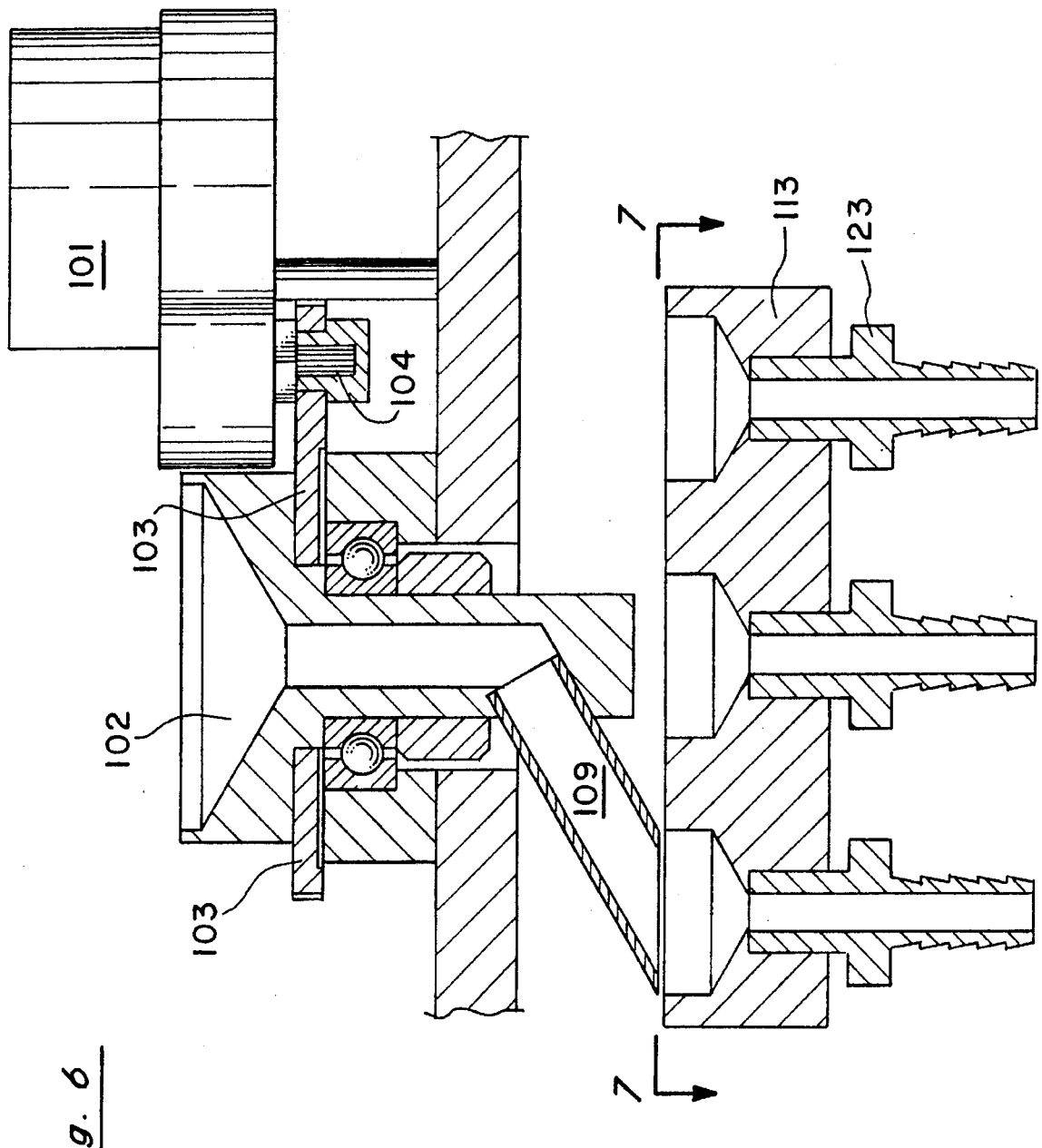
FIG. 6 is a side cross-sectional view of the column select funnel assembly used to direct wear particles to selected regions on the membrane filter 135.
Figure 7:
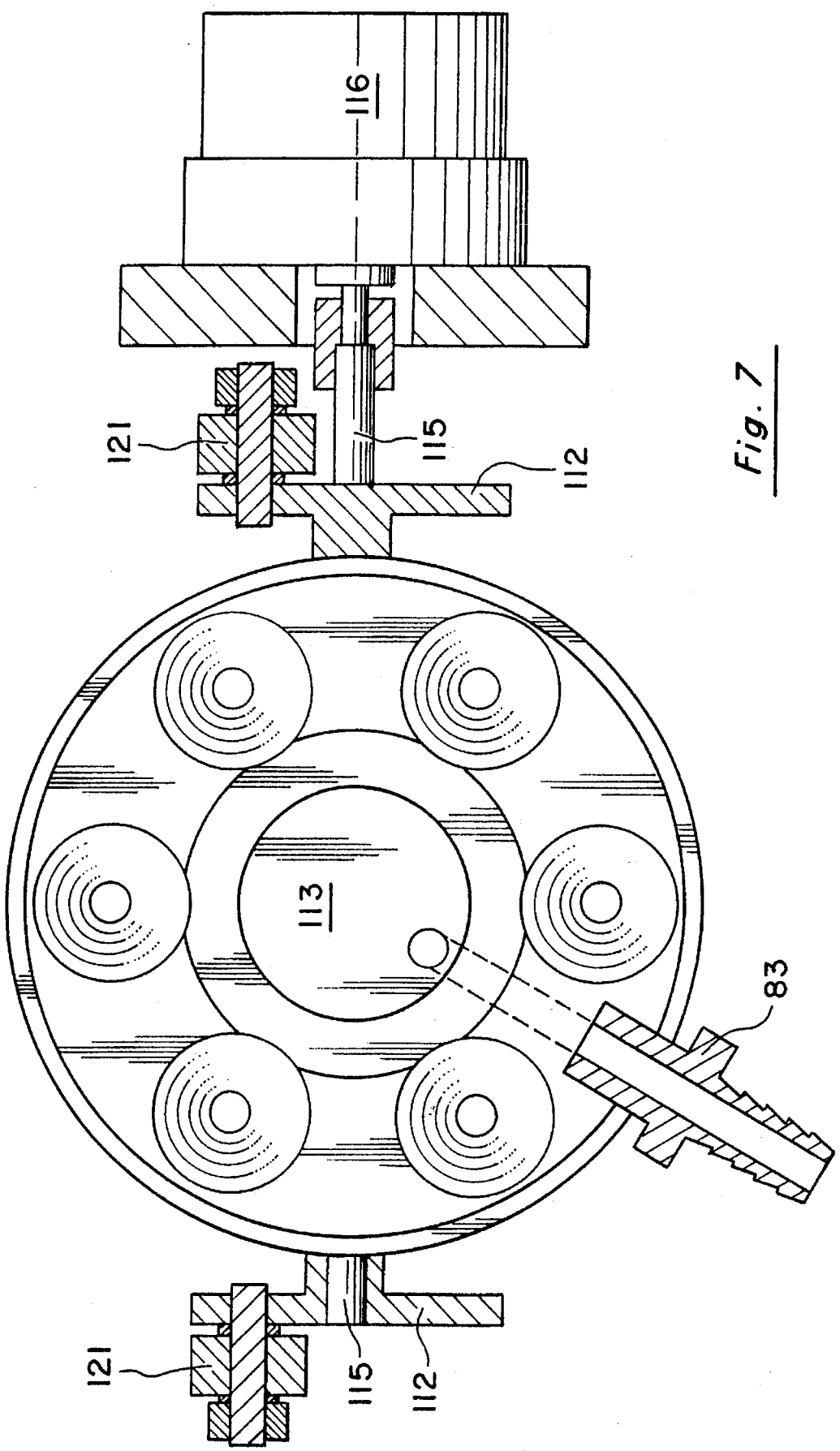
FIG. 7 is a top view of the funnel control plate corresponding to FIG. 6.
Figure 8:
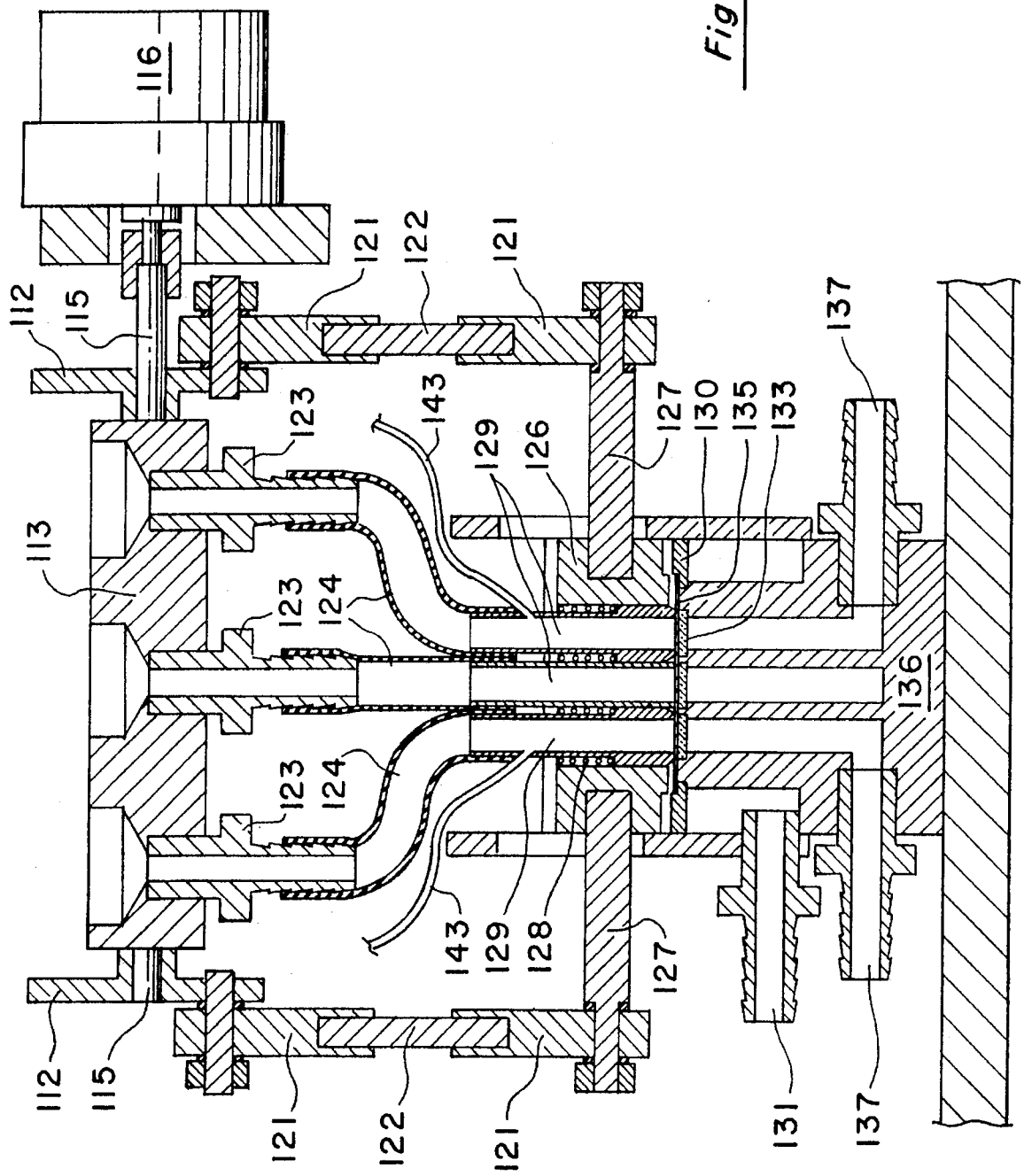
FIG. 8 is a side cross-sectional view of the column assembly used to hold the membrane filter 135.

FIGS. 6–8 depict the remaining stages of the particle size separation system in sequential order. The column selection assembly shown in FIG. 6 directs solvent and wear particles exiting the particle traps into a selected column to create a plurality of samples on different portions of the membrane filter 135. This flow is gathered by the column select funnel 102 and is routed to a selected funnel on the funnel plate 113 through the outlet tube 109. Each of the funnels is connected to a corresponding column in the filtration assembly (described below) via an outlet connector 123 and a flexible tube 124, as shown in FIG. 8. The entire column selection assembly is rotated about a vertical axis by means of a motor 101 and gear train 103, 104.

FIG. 7 is a corresponding top view of the funnel plate 113 and the mechanism used to raise and lower the filtration column assembly relative to the membrane filter 135. FIG. 8 provides a cross-sectional view of the funnel plate 113 and the filtration column assembly beneath. Based on the position of the outlet tube 109, solvent and wear particles can be selectively directed to any one of the funnels in the funnel plate 113 and into a corresponding filtration column 129 to create a series of samples on the membrane filter 135. The motor 116, shafts 115 and 127, and linkages 121 and 122 are used to raise and lower the filtration column assembly to permit installation and removal of the membrane filter 135 and its carrier 130. Evacuation ports 137 allow a pressure differential to be created across the membrane filter to accelerate filtration. Particle retention fluid is automatically dispensed through an inlet tube 143 into each of the filtration columns 129 to secure the particles to the surface of the membrane filter 135. An overflow port 131 drains any excess fluid. The holding tank also receives excess fluid created by operator error or operational failure (e.g., if the membrane filter plugs). The holding tank drains into the same vacuum waste canister 192 that draws the filtered fluid through the membrane filter, as shown in FIG. 1. The particle size separation system also includes design features: to flush extracted particles from the collection surfaces of the particle traps; to dispose of excess fluid that overfills any of the individual filtration columns; to collect the excess fluid into a waste container for disposal; and to select the specific location for deposition of a size range or type of particle (e.g., magnetic or non-magnetic).

Particle Trap Operation Sequence.

At the beginning of each sample preparation sequence, the outlet of the column select funnel 102 is positioned directly above the center of the first funnel of the funnel plate 113 while the upper column block 126 has been moved to the position where all of the filtration columns 129 have created a fluid-tight seal, and are in contact with the membrane filter 135. The filtration columns 129 mounted within upper column block 126 are moved into intimate contact with membrane filter 135 by activation of a motor 116. The first funnel of the funnel plate 113 corresponds to the first filtration column 129. This position will be the location where the fine non-magnetic particles will be deposited on the membrane filter 135.

As the non-magnetic particles are flushed through the magnetic separation system, they enter the particle size separation system through the inlet funnel 90 to the particle traps. Prior to insertion of the oil filter 20, the mounts 95 for the screen sieves 96 of both particle trap assemblies are rotated by their respective motors 99 to be sealed across the internal diameter of the main passage of the particle trap housing 94. Any coarse non-magnetic wear particles are retained by the coarse particle trap and medium non-magnetic particles are retained by the medium particle trap. Only fine non-magnetic particles pass through both particle traps and are deposited on a selected portion of the membrane filter 135 to create a first sample.

When all of the fluid and the fine wear particles have been forced through the particle trap assemblies and into the first filtration column 129, the column select motor 101 is activated to drive gears 104 and 103 which rotate the outlet tube 109 to a position centered directly above the second funnel of the funnel plate 113 which corresponds to the second filtration column 129 and the location of the second deposit of extracted particles on the membrane filter 135. The medium screen sieve 96 is rotated 90 degrees by the motor 99 to its second position in which the medium screen sieve unblocks the passage. The coarse screen sieve remains in its first position. The rinse sequence is repeated to minimize cross contamination between samples and to flush extracted particles through all previous systems. This also provides a quantity of fluid to effectively dislodge any medium-size particles from the medium screen sieve and the remaining components of the particle trap assemblies. The multiport solvent valve 188 is then switched to connect the pressurized solvent line to each of the nozzles 84 used for rinsing the particle traps and the multiport control valve 204 is opened to allow solvent to rinse medium-size particles from the surfaces of the screen sieve 96, mount 95, O-ring 100, and the interior surfaces of the main housing 94 of the particle trap. These medium particles are carried downstream and are deposited on a second sample portion of the filter membrane 135.

The coarse screen sieve 96 is then rotated 90 degrees by the motor 99 to its second position in which the coarse screen sieve unblocks the passage. This sequence described above is repeated to deposit a third sample on the filter membrane 135 consisting of coarse non-magnetic particles.

Following deposition of the small, medium, and coarse nonmagnetic particles as disclosed above, the magnetic particles motor 75 is activated by the control system to move the magnets 77 away from the glass tube 79. The rinse sequence is repeated to minimize cross contamination between samples and to flush magnetic particles into the inlet funnel 90 to the particle traps. The operation sequence for separating the size ranges of extracted particles and depositing the magnetic particles onto the membrane filter 135 is identical to the sequence discussed above with the exception that the smallest magnetic particles are directed to the fourth position of the funnel plate 113 and are deposited in the fourth position of the membrane filter 135. Similarly, medium magnetic particles are directed to the fifth position of the funnel plate 113 and are deposited in the fifth position of the membrane filter 135. The coarse magnetic particles are directed to the sixth position of the funnel plate 113 and are deposited in the sixth position of the membrane filter 135.

Collection and Disposal of Excess Fluid.

The funnel plate has six individual funnels that serve as a means to introduce extracted particles and fluids to the six individual filtration columns 129 used to deposit the extracted particles onto the surface of the membrane filter 135. In the event that excessive quantities of extracted particles cause blockage of the pores of the membrane filter 135, or if excessive quantities of fluid are presented, each of the individual small funnels of the funnel plate 113 intersects the large central funnel which is designed to accept the overflow. The outlet port 83 of the central funnel of the funnel plate 113 serves as the drain for the funnel plate and is drained into the common vacuum waste canister 192 provided for collection of all fluids by actuation of valve 152.

Filtration System.

As shown in FIG. 8, a slidable carrier 130 and a frame hold the membrane filter and provide precise registration between the individual filtering columns and the membrane filter and easy handling of the membrane filter. The slidable carrier 130 is locked in position during filtering. A support ring is added to the membrane filter 135 to aid registration and provide ease of handling while maintaining cleanliness of the membrane filter. The support ring also provides a means of handling the membrane filter 135 without disturbing the particle sample deposits to be analyzed.

Operation of this system is described from the point after the membrane filter 135 and oil filter 20 have already been installed. The upper column block 126 has already been lowered into contact with the membrane filter 135 by the rotation of the shaft 115 driven by motor 116, as illustrated in FIG. 8. To accomplish the lowering motion, the mount 112 for the rod end is used as an offset cam attached to the shaft 115. The rod ends 121 are joined through a connector 122 attached to the upper column block 126 through a shaft 127, thus converting the rotational motion of the shaft 115 into linear motion.

The membrane filter 135 is supported by the lower column block 136. Fritted glass disks 133 provide support for the membrane filter 135 in those areas where fluid will be drawn through by vacuum lines. To seal the surface around the fritted glass disks 133, a seal is bonded to the top surface of the lower column block 136 having openings aligned with the fritted glass disks 133 and the filtration columns 129 supported by the upper column block 126. The top of each filtration column 129 is connected by a flexible tube 124 that is compatible with the fluids to be used. The other end of the flexible tube 124 is connected to the funnel outlet 123 on the underside of funnel plate 113 to complete the fluid path.

The filtration columns 129 are mounted within the upper column block 126 with a spring 128. The spring 128 ensures that the filtration column 129 extends beyond the lower edge of upper column block 126 and exerts sufficient force on the membrane filter 135 to provide a fluid-tight seal. The spring 128 begins to be compressed when the filtration column 129 makes contact with the membrane filter 135, which is well before the lowest point of travel attained by the upper column block 126.

Each of the individual filtration columns 129 has a separate column evacuation port 137 and a valve 155 in line to the vacuum waste canister 192. This allows the vacuum pump 144 to evacuate the air from the vacuum waste canister 192 causing fluids to be drawn into the canister without being drawn through vacuum pump 144. After all fluids have been drawn through the filtration columns 129, the retention fluid valve 187 is opened and a few drops of highly diluted fluid are dispensed from the pressurized retention fluid reservoir system through an inlet tube 143 to complete the filtration process. An overflow drain 131 allows any remaining fluid to be drawn into the vacuum waste canister by actuation of a valve 153. Fluids could enter this area if damage occurred to the filtration column 129 or if wear particles prevented proper sealing. Also, if the membrane filter 135 becomes clogged and fluid is unable to pass through, residual fluid remaining on top of the membrane filter 135 will drain into the vacuum waste canister 192 through the overflow drain 131 and valve 153.

Figure 9:
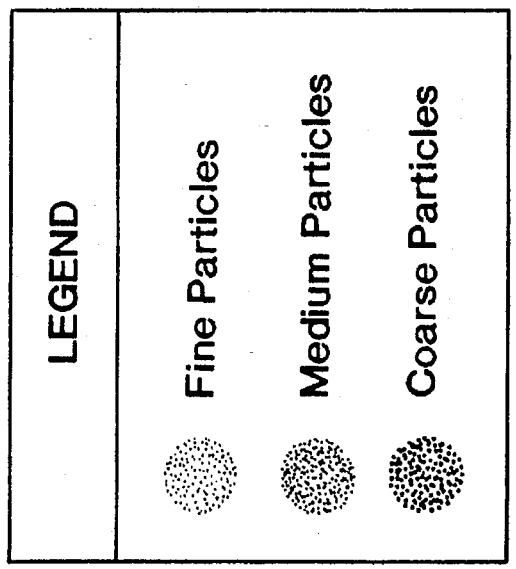
FIG. 9 is a top view of a membrane filter showing six sample spots.
Figure 9:
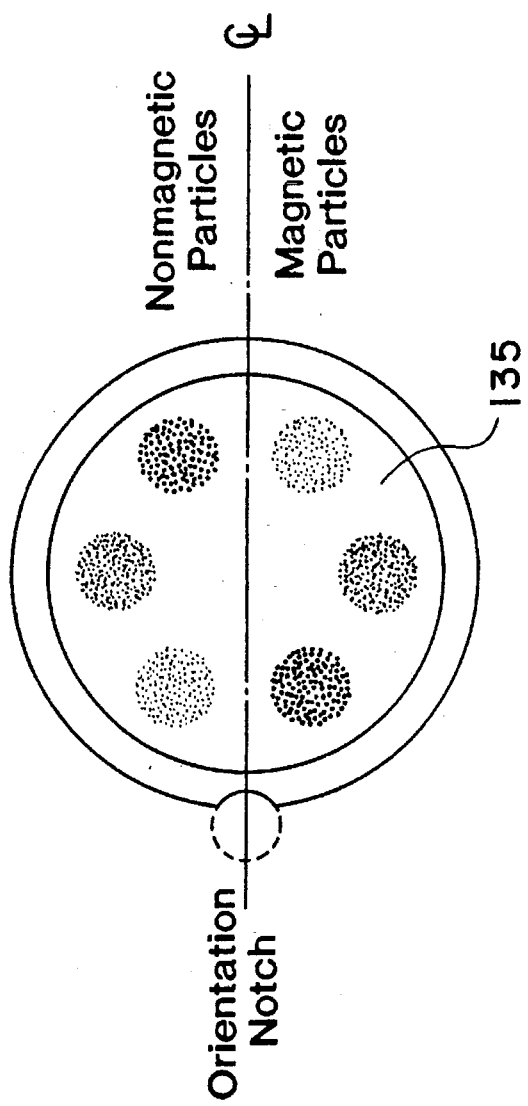

When the sample preparation sequence is completed, the control system actuates the motor 116 to release the membrane filter carrier 130 and an indicator is illuminated. This completes the sample preparation sequence and the membrane filter 135 is now ready for analysis by the EDXRF system. The resulting membrane filter with six deposited samples is shown in FIG. 9. The non-magnetic wear particles in the sample are separated by size ranges into coarse, medium, and fine categories in the upper three samples, and the magnetic wear particles are separated into coarse, medium, and fine categories in the lower three samples in FIG. 9.

Fluid Checks.

As a precaution to avoid insufficient quantities of fluids or inadequate volume to contain collected fluid in the vacuum waste canister 192, a number of level sensors 166, 167, and 168 are included in the system. Each level sensor has a corresponding indicator to alert the operator prior to the start of a sample preparation sequence. If any of these indicators have been illuminated prior to the start of a sample preparation sequence, an indicator will remain illuminated until the operator has installed additional fluids or drained the waste container as indicated. If a level sensor 166, 167, or 168 reaches the switch point during a sample preparation sequence, the appropriate corresponding indicator will immediately be illuminated, but the preparation of the sample in progress will not be interrupted. The set points for each level sensor 166, 167, and 168 are selected to ensure that adequate volume remains in the vacuum waste canister 192 to complete the sample preparation cycle without depletion of fluid or overfilling the vacuum waste canister 192. At any time when the vacuum waste canister 192 may be emptied, the valve 161 to the drain waste container is opened by the control system. If desired by the operator, a manual drain waste valve can then be opened, allowing collected fluid wastes to be drained from the sample preparation system into an external storage container for proper disposal.

During each system reset, the control system will automatically activate the vacuum pump 144 and control valves 201 and 202. This process creates a partial vacuum on the internal solvent reservoir 191 and the retention fluid reservoir 190, allowing fluids from external supply reservoirs to refill the internal reservoirs through check valves 196 and 197. The maximum activation time allowed by the control system for the vacuum pump 144 and control valves 201 and 202 is sufficient to refill the internal reservoirs. When the control system receives a signal from the top solvent level sensor 166, the control valve 202 is turned off. Likewise, when the control system receives a signal from the top retention fluid level sensor 167, the control valve 201 is turned off. The pressure pump 145 is turned on for a few seconds to ensure that adequate pressure exists, thereby forcing both of the check valves 196 and 197 to close. This automated sequence is a safety feature designed to minimize operator handling and potential spills of solvent and particle retention fluid while ensuring that the supply of required fluids is always adequate.

The above disclosure sets forth a number of embodiments of the present invention. Other arrangements or embodiments, not precisely set forth, could be practiced under the teachings of the present invention and as set forth in the following claims.

We claim:

1. A system for preparing samples of wear particles comprising:

a filter;

a housing having a passage with an inlet for receiving a flow of wear particles suspended in a fluid and an outlet;

at least one particle trap having openings for retaining wear particles larger than a predetermined size and for passing fluid and wear particles smaller than said size, with mounting means for selectively moving said particle trap between a first position in which said particle trap substantially blocks said housing passage while said flow of wear particles and fluid is introduced into said inlet, and a second position in which said passage is substantially unblocked by said particle trap;

means for rinsing wear particles from said particle trap in said second position; and means for selectively directing said flow from said outlet of said housing onto at least a first sample portion of said filter when said particle trap is in said first position, and onto at least a second sample portion of said filter when said particle trap is in said second position.

2. The sample preparation system of claim 1, wherein said particle trap comprises a screen.

3. The sample preparation system of claim 1, further comprising means for selectively creating a magnetic field to retain magnetic wear particles upstream from said particle trap.

4. The sample preparation system of claim 3, further comprising an inlet tube upstream from said particle trap, and wherein said means for selectively creating a magnetic field comprises:

at least one magnet; and means for selectively moving said magnet between a first position adjacent to said tube and a second position remote from said tube.

5. The sample preparation system of claim 1, further comprising a trap for preventing oversize wear particles from entering said passage.

6. The sample preparation system of claim 1, further comprising:

a coarse particle trap;

a medium particle trap; and control means for controlling said particle traps, said rinsing means, and said flow directing means in the following sequence of steps:
 (a) initially positioning both of said particle traps to block said passage so that only fine wear particles in said flow are directed onto a first sample portion of said filter;
 (b) moving said medium particle trap to unblock said passage and rinsing wear particles from said medium particle trap so that only medium wear particles are directed onto a second sample portion of said filter; and
 (c) moving said coarse particle trap to unblock said passage and rinsing wear particles from said coarse particle trap so that only coarse wear particles are directed onto a third sample portion of said filter.

7. The sample preparation system of claim 1, further comprising means for applying a retention fluid to said samples on said filter.

8. The sample preparation system of claim 1, further comprising means for creating a pressure differential across said filter to accelerate filtration.

9. A system for preparing samples of wear particles separated by particle size comprising:

a filter having a plurality of portions for receiving wear particle samples;

a housing having a passage with an inlet for receiving a flow of wear particles suspended in a fluid and an outlet;

a coarse particle trap having openings for retaining wear particles larger than a predetermined coarse size and for passing fluid and wear particles smaller than said coarse size, said coarse particle trap also including mounting means for selectively moving said coarse particle trap between a first position in which said coarse particle trap substantially blocks said housing passage and a second position in which said passage is substantially unblocked by said coarse particle trap;

means for rinsing said coarse wear particles from said coarse particle trap in said second position;

a medium particle trap having openings for retaining wear particles larger than a predetermined medium size and for passing fluid and wear particles smaller than said medium size, said medium particle trap also including mounting means for selectively moving said medium particle trap between a first position in which said medium particle trap substantially blocks said housing passage downstream from said coarse particle trap and a second position in which said passage is substantially unblocked by said medium particle trap;

means for rinsing said medium wear particles from said medium particle trap in said second position;

means for selectively directing said flow from said outlet of said housing onto a selected sample portion of said filter; and control means for controlling said particle traps, said rinsing means, and said flow directing means in the following sequence of steps:
 (a) initially positioning both of said particle traps to block said passage so that only wear particles in said flow smaller than said medium size are directed onto a first sample portion of said filter;
 (b) moving said medium particle trap to unblock said passage and rinsing wear particles from said medium particle trap so that only medium wear particles are directed onto a second sample portion of said filter; and
 (c) moving said coarse particle trap to unblock said passage and rinsing wear particles from said coarse particle trap so that only coarse wear particles are directed onto a third sample portion of said filter.

10. The sample preparation system of claim 9, further comprising means for selectively creating a magnetic field to retain magnetic wear particles upstream from said particle trap.

11. The sample preparation system of claim 10, further comprising an inlet tube upstream from said particle trap, and wherein said means for selectively creating a magnetic field comprises:

at least one magnet; and means for selectively moving said magnet between a first position adjacent to said tube and a second position remote from said tube.

12. The sample preparation system of claim 10, wherein said control means further controls said magnetic field means in the following sequence of steps:
 (a) initially creating a magnetic field to retain magnetic wear particles within said tube so that at least three samples are prepared containing non-magnetic coarse, medium, and fine wear particles; and
 (b) subsequently releasing said magnetic wear particles so that at least three samples are prepared containing magnetic coarse, medium, and fine wear particles.

13. The sample preparation system of claim 9, further comprising a trap for preventing oversize wear particles from entering said passage.

14. The sample preparation system of claim 9, wherein said particle traps comprise a screen.

15. The sample preparation system of claim 9, further comprising means for applying a retention fluid to said samples on said filter.

16. A system for preparing samples of wear particles separated by particle size and magnetic characteristics comprising:

a filter having a plurality of portions for receiving wear particle samples;

a passage having an inlet for receiving a flow of wear particles suspended in a fluid and an outlet;

means for selectively creating a magnetic field within said passage to retain magnetic wear particles;

a coarse particle trap downstream from said magnetic field means having openings for retaining wear particles larger than a predetermined coarse size and for passing fluid and wear particles smaller than said coarse size, said coarse particle trap also including mounting means for selectively moving said coarse particle trap between a first position in which said coarse particle trap substantially blocks said housing passage and a second position in which said passage is substantially unblocked by said coarse particle trap;

means for rinsing said coarse wear particles from said coarse particle trap in said second position;

a medium particle trap having openings for retaining wear particles larger than a predetermined medium size and for passing fluid and wear particles smaller than said medium size, said medium particle trap also including mounting means for selectively moving said medium particle trap between a first position in which said medium particle trap substantially blocks said housing passage downstream from said coarse particle trap and a second position in which said passage is substantially unblocked by said medium particle trap;

means for rinsing said medium wear particles from said medium particle trap in said second position;

means for selectively directing said flow from said outlet of said housing onto a selected sample portion of said filter; and control means for controlling said particle traps, said rinsing means, and said flow directing means in the following sequence of steps:

(a) initially activating said magnetic field means and positioning both of said particle traps to block said passage so that only non-magnetic wear particles in said flow smaller than said medium size are directed onto a first sample portion of said filter;

(b) moving said medium particle trap to unblock said passage and rinsing wear particles from said medium particle trap so that only medium non-magnetic wear particles are directed onto a second sample portion of said filter;

(c) moving said coarse particle trap to unblock said passage and rinsing wear particles from said coarse particle trap so that only coarse non-magnetic wear particles are directed onto a third sample portion of said filter;

(d) positioning both of said particle traps to block said passage, deactivating said magnetic field means, and rinsing said magnetic wear particles onto said particle traps, so that only magnetic wear particles smaller than said medium size are directed onto a fourth sample portion of said filter;

(e) moving said medium particle trap to unblock said passage and rinsing said magnetic wear particles from said medium particle trap so that only medium magnetic wear particles are directed onto a fifth sample portion of said filter; and (f) moving said coarse particle trap to unblock said passage and rinsing said magnetic wear particles from said coarse particle trap so that only coarse magnetic wear particles are directed onto a sixth sample portion of said filter.

17. The sample preparation system of claim 16, wherein said particle traps comprise a screen.

18. The sample preparation system of claim 16, wherein said means for selectively creating a magnetic field within said passage comprises at least one magnet and means for selectively moving said magnet between a first position adjacent to said passage and a second position remote from said passage.

19. The sample preparation system of claim 16, further comprising means for applying a retention fluid to said samples on said filter.

20. The sample preparation system of claim 16, further comprising a trap for preventing oversize wear particles from entering said passage.

* * * * *